United States Patent
Addison et al.

(10) Patent No.: US 10,765,344 B2
(45) Date of Patent: Sep. 8, 2020

(54) MEASURING RESPIRATORY PARAMETERS FROM AN ECG DEVICE

(71) Applicant: COVIDIEN LP, Mansfield, MA (US)

(72) Inventors: Paul Stanley Addison, Edinburgh (GB); Daniel Wayne Bartlett, York Haven, PA (US); James N. Watson, Edinburgh (GB)

(73) Assignee: Covidien LP, Mansfield, MA (US)

( * ) Notice: Subject to any disclaimer, the term of this patent is extended or adjusted under 35 U.S.C. 154(b) by 157 days.

(21) Appl. No.: 15/801,955

(22) Filed: Nov. 2, 2017

(65) Prior Publication Data
US 2019/0125214 A1    May 2, 2019

(51) Int. Cl.
| | |
|---|---|
| *A61B 5/01* | (2006.01) |
| *A61B 5/091* | (2006.01) |
| *A61B 5/0456* | (2006.01) |
| *A61B 5/053* | (2006.01) |
| *A61B 5/00* | (2006.01) |

(52) U.S. Cl.
CPC ............ *A61B 5/091* (2013.01); *A61B 5/0456* (2013.01); *A61B 5/053* (2013.01); *A61B 5/4839* (2013.01); *A61B 5/7278* (2013.01); *A61B 5/746* (2013.01)

(58) Field of Classification Search
None
See application file for complete search history.

(56) References Cited

U.S. PATENT DOCUMENTS

2016/0331273 A1* 11/2016 Armoundas ............. A61B 5/72

* cited by examiner

*Primary Examiner* — Eric F Winakur
*Assistant Examiner* — Marjan Fardanesh

(57) ABSTRACT

Methods, systems, and devices for measuring respiratory parameters from an ECG device are described. The method may include receiving an electrocardiogram (ECG) signal associated with a patient. The method may further include detecting a change in modulation of the ECG signal between a first portion of the ECG signal and a second portion of the ECG signal. The method may further include determining a change in respiratory effort of the patient based at least in part on the change in modulation.

16 Claims, 12 Drawing Sheets

MEASURING RESPIRATORY PARAMETERS FROM AN ECG DEVICE

BACKGROUND

The following relates generally to physiological monitoring of a patient and more specifically to measuring respiratory parameters from an electrocardiogram (ECG) device.

In a healthcare facility such as a hospital, respiratory parameters of a patient may be monitored by one or more medical devices. For example, an ECG device may be used to measure a patient's respiratory rate and transthoracic impedance (TTI), and the TTI measurement may be used to determine a tidal volume (TV) of the patient's lungs. Although a patient's respiratory rate and TV may be determined using an ECG device, these parameters alone may be of limited use when monitoring the respiratory function of a patient.

SUMMARY

The described features generally relate to methods, systems, devices, or apparatuses that support measuring respiratory parameters from an electrocardiogram (ECG) device In addition to determining a patient's respiratory rate, transthoracic impedance (TTI), and tidal volume (TV), an ECG device may be used to determine a measure of respiratory effort of a patient. For example, changes in amplitude and frequency modulations in an ECG signal may be used to detect changes in a patient's respiratory effort over time. Changes in respiratory effort, in combination with respiratory rate and TV, may be used to indicate the onset or progression of certain disease statuses. In some examples, a system may be configured to diagnose a disease status based on a combination of these respiratory parameters and titrate a drug corresponding to the disease status.

Methods and apparatuses are described for patient monitoring. A method may include receiving an ECG signal associated with a patient. The method may also include detecting a change in modulation of the ECG signal between a first portion of the ECG signal and a second portion of the ECG signal. Additionally, the method may include determining a change in respiratory effort of the patient based at least in part on the change in modulation.

In some embodiments, detecting the change in modulation comprises comparing an R-wave amplitude modulation of a first plurality of R-waves from the first portion of the ECG signal with an R-wave amplitude modulation of a second plurality of R-waves from the second portion of the ECG signal. In some embodiments, the R-wave amplitude modulation of the second plurality of R-waves is greater than the R-wave amplitude modulation of the first plurality of R-waves.

In some embodiments, detecting the change in modulation comprises comparing a frequency modulation of a first plurality of R-waves from the first portion of the ECG signal with a frequency modulation of a second plurality of R-waves from the second portion of the ECG signal. In some embodiments, a difference between a maximum R-wave frequency and a minimum R-wave frequency in the second portion of the ECG signal is greater than a difference between a maximum R-wave frequency and a minimum R-wave frequency in the first portion of the ECG signal.

In some embodiments, detecting the change in modulation comprises comparing a baseline of a first plurality of R-waves from the first portion of the ECG signal with a baseline of a second plurality of R-waves from the second portion of the ECG signal. In some embodiments, the method may include detecting an increase in modulation strength in the second portion of the ECG signal. In some embodiments, the method may include determining an increase in respiratory effort by the patient based at least in part on the increase in modulation strength.

In some embodiments, the method further comprises determining a respiratory effort measure of the patient based at least in part on the change in respiratory effort. In some embodiments, the method may include comparing the respiratory effort measure to a predetermined respiratory effort threshold. In some embodiments, the method may include determining a change in a respiratory condition of the patient based at least in part on the comparison.

In some embodiments, the method may include determining a TTI of the patient. The method may include determining a change in a tidal volume of the patient based at least in part on the TTI, wherein determining the change in the respiratory condition of the patient is based at least in part on the change in the tidal volume.

In some embodiments, the method may include determining a respiratory rate of the patient based at least in part on the ECG signal. The method may include comparing the respiratory rate to a predetermined respiratory rate threshold, wherein determining the change in the respiratory condition of the patient is based at least in part on the respiratory rate.

In some embodiments, the method may include determining whether to administer a drug to the patient based at least in part on the comparison. Additionally, the method may include automatically administering the drug based at least in part on the determination. In some embodiments, the method may include triggering an alarm indicating the change in respiratory effort of the patient.

DETAILED DESCRIPTION

Figure 1:
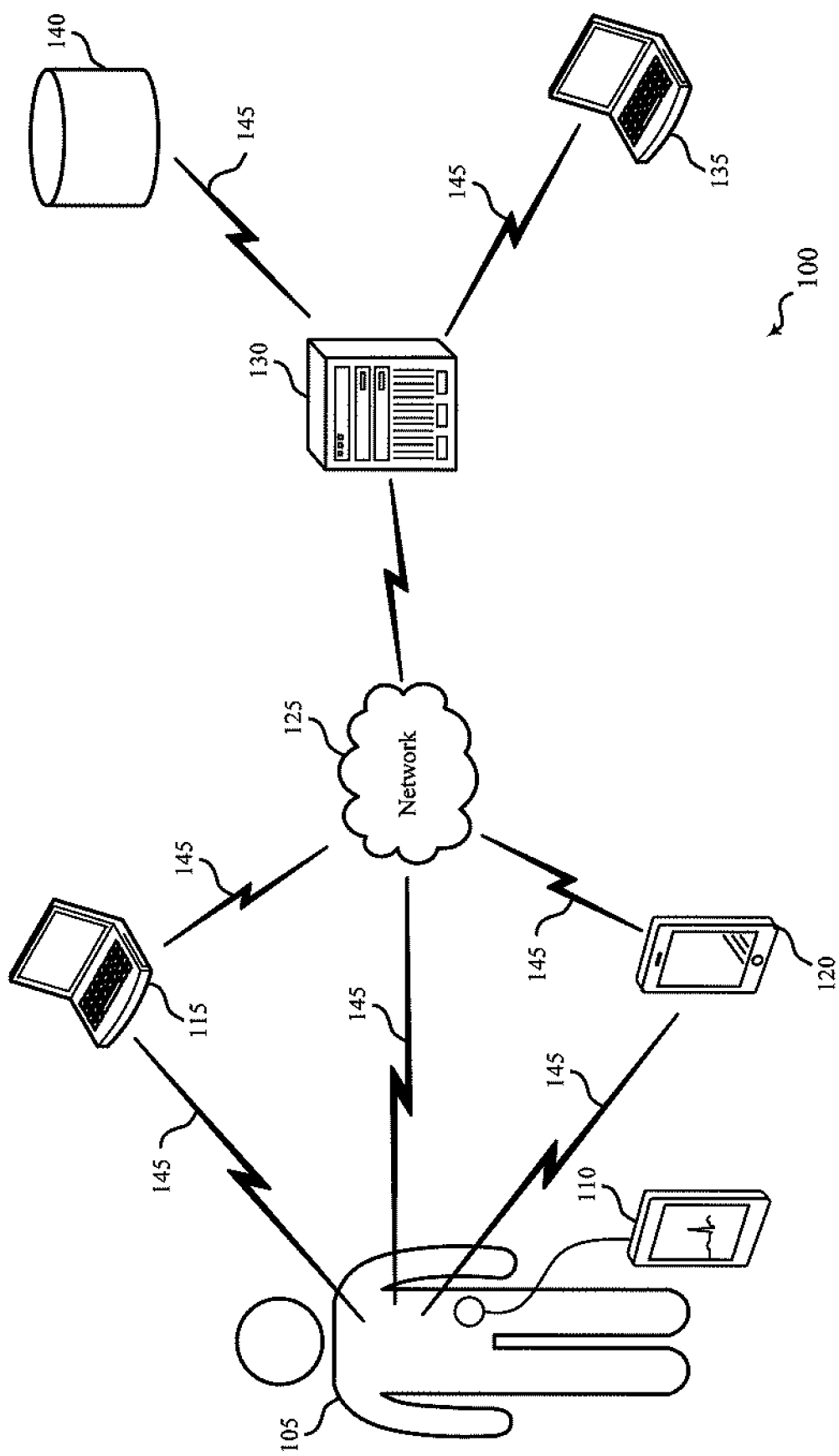
FIG. 1 illustrates an example of a patient monitoring system that supports measuring respiratory parameters from an ECG device in accordance with aspects of the present disclosure.

An electrocardiogram (ECG) device may record the electrical activity of the heart over a period of time. A graphical plot of the electrical activity as a function of time may be used to calculate, indicate, or otherwise determine physiological parameters pertinent to respiratory function. For example, as described in more detail below, a patient's respiratory rate and a measure of respiratory effort (or changes in respiratory effort) may be indicated by patterns in the plot (e.g., frequency and amplitude modulations). A patient's transthoracic impedance (TTI) may be determined from the leads of the ECG device itself, and a measure of the patient's tidal volume (TV) may be derived from the TTI measurement. Respiratory effort, in combination with respiratory rate and TV, may be used to indicate respiratory function or to diagnose certain respiratory diseases. Examples of respiratory diseases that may be indicated by an ECG signal include, but are not limited to, pneumonia, asthma, chronic obstructive pulmonary disease (COPD), sleep anemia, and pulmonary edema. A system may be configured to automatically titrate medication or some other form of treatment corresponding to the diagnosis or alert a clinician of the diagnosis.

The waveform of an ECG signal may modulate according to amplitude and frequency. Amplitude modulation may be referred to as a change in strength of certain features of the ECG signal over time (e.g., changes in the height patterns of R-waves over time). Similarly, frequency modulation may be referred to as a change in the frequency of occurrence of certain features of the ECG signal over time (e.g., changes in the frequency of R-waves over time). A patient's respiratory rate may be determined from frequency or amplitude modulations in the ECG signal by determining points of inhalation and exhalation from the ECG signal. In a similar fashion, a patient's respiratory effort (or at least changes in respiratory effort) may be determined by detecting points of increased breathing resistance that are indicated by frequency or amplitude modulations in the ECG signal.

The combination of respiratory rate, respiratory effort, and TV may be used to differentiate patient disease status. For example, a fast respiratory rate, a low TV (i.e., indicated by shallow breathing), and an increased respiratory effort may indicate pneumonia. Similarly, a low respiratory rate, a high TV, and an increased respiratory effort may indicate an asthmatic episode. The combination of respiratory rate, respiratory effort, and TV may be used by a system to titrate a drug (or some other form of medicinal treatment) corresponding to the disease status indicated by these parameters. For example, if respiratory rate, respiratory effort, and TV are greater or less than a prescribed threshold, then the system may titrate a drug to treat the patient based on the diagnosis.

Aspects of the disclosure are initially described in the context of a patient monitoring system. Aspects of the disclosure are further illustrated by and described with reference to an exemplary ECG diagram illustrating measuring respiratory parameters from an ECG device. Aspects of the disclosure are further illustrated by and described with reference to apparatus diagrams, system diagrams, and flowcharts that relate to respiration analysis.

FIG. 1 illustrates an example of a patient monitoring system 100 that supports measuring respiratory parameters from an ECG device in accordance with aspects of the present disclosure. The patient monitoring system 100 may include a patient 105 wearing, carrying, or otherwise coupled with a medical device 110. Although a single medical device 110 is shown, multiple medical devices 110 may be coupled to the patient 105. The patient 105 may be a patient in a hospital, nursing home, home care, a medical facility, or another care facility. The medical device 110 may transmit signals via wired or wireless communications links 145 to local computing devices 115, 120 or to a network 125.

The medical device 110 may include one or more sensors configured to collect a variety of physiological parameters as well as information related to movement of the patient 105. For example, the medical device 110 may include a pulse oximetry (SpO2) sensor, a capnography sensor, a heart rate sensor, a blood pressure sensor, an ECG sensor, a respiratory rate sensor, a glucose level sensor, a depth of consciousness sensor, a body temperature sensor, an accelerometer, or any other sensor configured to collect physiological or motion data associated with the patient 105. In some cases, medical device 110 may be an example of an ECG device. The ECG device may be coupled to a device configured to administer a drug to the patient 105 manually or automatically in response to one or more respiratory parameters derived from the ECG device. In some cases, if a drug is already being administered to the patient (e.g., analgesics or narcotics), the device may be configured to reduce or cease administration of the drug in response to the derived respiratory parameters.

The medical device 110 may be coupled with the patient 105 in a variety of ways depending on the data being collected. For example, the medical device 110 may be directly coupled with the patient 105 (e.g., physically connected to the patient's chest, worn around the patient's wrist, attached to the patient's finger, or positioned over the patient's nose or mouth). The medical device 110 may also be coupled with the patient 105 via a transmission line that sends the signals from the patient to the medical device 110. The data collected by the medical device 110 may be wired or wirelessly transmitted to either the computing devices 115 or to the remote computing device 135 (via the network 125 and central station 130). Data transmission may occur via, for example, frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc.).

Local computing device 115, 120 may be a wireless device such as a tablet, cellular phone, personal digital assistant (PDA) a dedicated receiver, or other similar device or a spatially distributed network of devices configured to receive signals from the medical device 110. Computing device 115, 120 may be a wireless laptop computer, a clinician Workstation on Wheels, or a smart hospital bed configured to receive signals from the medical device 110. The computing devices 115, 120 may be in communication with a central station 130 via network 125.

The medical device 110 may also communicate directly with the central station 130 via the network 125. The central station 130 may be a server or a central nurse station located within the hospital or in a remote location. The central station 130 may be in further communication with one or more remote computing devices 135, thereby allowing a clinician to remotely monitor the patient 105. The central station 130 may also be in communication with various remote databases 140 where the collected patient data may be stored. In some cases, the remote databases 140 include electronic medical records (EMR) applications for storing and sharing patient data.

In accordance with various embodiments, methods and apparatuses are described for collecting data associated with a respiratory function of the patient 105 using one or more medical devices 110. Medical device 110 may additionally be utilized to detect non-respiratory physiological data, such as body mass index, posture, motion, medication, or congestive heart failure, among others. In other examples, the non-respiratory physiological data may be collected from caregiver input at local computing devices 115, 120 or remote computing device 135; may be collected from central station 130; or may be collected from remote database 140, such as from the patient's EMR.

Figure 2:
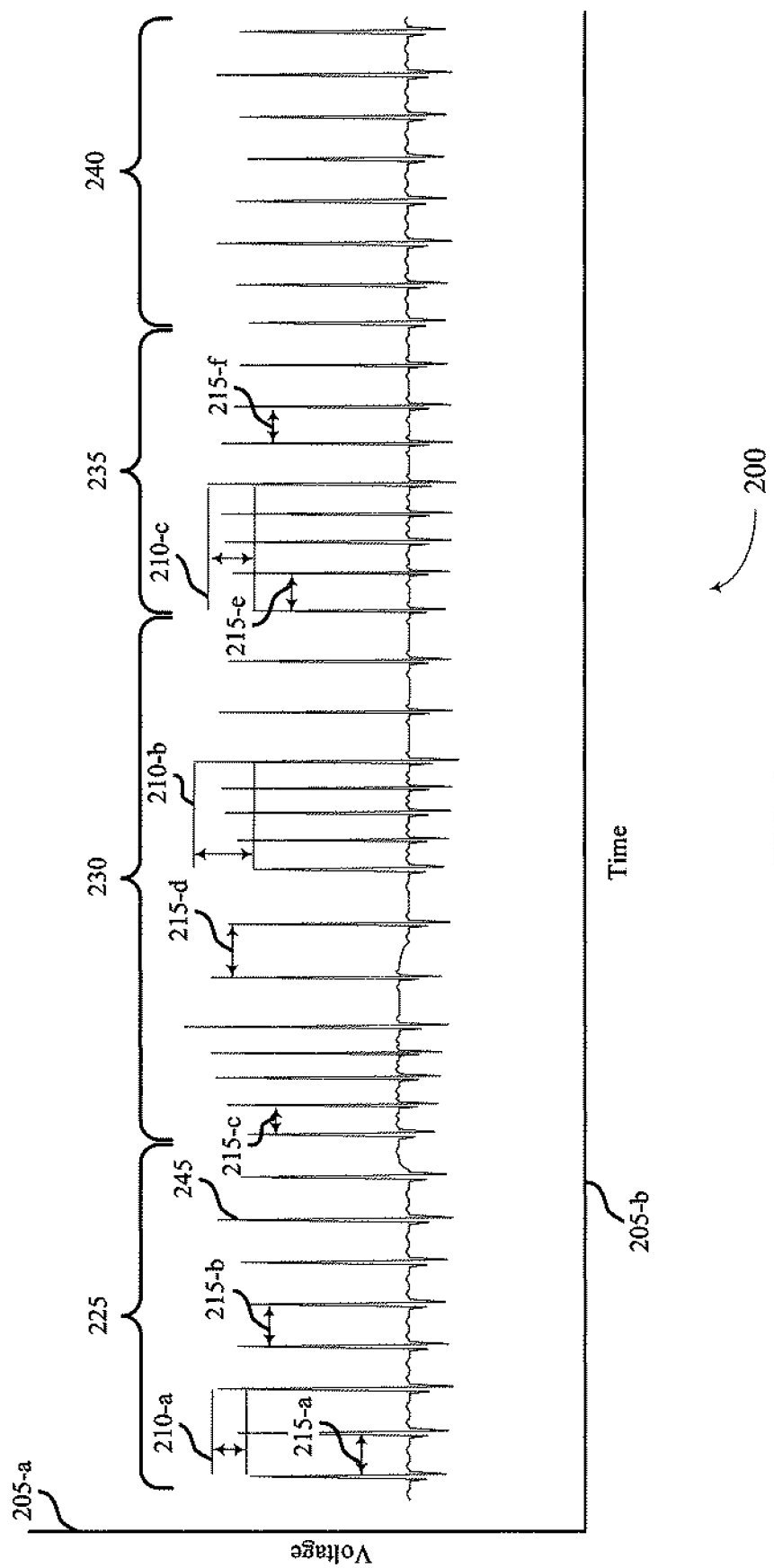
FIG. 2 illustrates an example diagram that supports measuring respiratory parameters from an ECG device in accordance with aspects of the present disclosure.

FIG. 2 illustrates an example diagram that supports measuring respiratory parameters from an ECG device in accordance with aspects of the present disclosure. Plot 200 may be an example ECG signal that depicts the voltage of the ECG signal, illustrated by axis 205-a, as a function of time, illustrated by axis 205-b. The waveform of the ECG signal is be caused by the depolarization and repolarization of the heart over a period of time. Although the ECG device may typically be used to measure cardiac functions, plot 200 may also be used to determine certain respiratory parameters by observing the changes in patterns in plot 200.

Plot 200 may include a plurality of R-waves 245. An R-wave 245 is illustrated as an upward deflection of the ECG signal and may represent the rapid depolarization of the right and left ventricles of the heart. An R-wave 245 may be characterized by an amplitude (or strength) with respect to a baseline voltage, and a plurality of R-waves 245 may be characterized by a frequency. In accordance with aspects of the present disclosure, patterns in the amplitude and frequency of the R-waves 245 over time may be used to determine certain respiratory parameters of a patient.

For example, as a patient breathes in, the lungs expand, and the frequency of the heartbeat generally increases. Conversely, when a patient breathes out, the lungs contract and the frequency of the heartbeat generally decreases. The relationship between the naturally occurring variation in a patient's heart rate that occurs during a breathing cycle may be referred to as respiratory sinus arrhythmia (RSA). As described in more detail below, the frequency modulation of the heartbeat caused by the inhalation and exhalation processes may be observed from the plot 200, and a patient's respiratory rate may be derived based on this frequency modulation.

A first portion 225 of the ECG signal may include a first plurality of R-waves 245 and may represent a patient breathing without resistance (e.g., normal breathing). The first R-wave 245 to the third R-wave 245 in the first portion 225 may represent a normal inhalation and the fourth R-wave 245 to the sixth R-wave 245 may represent a normal exhalation. A distance between first R-wave 245 and second R-wave 245 in portion 225 may represent a localized R-wave frequency 215-a, and a distance between fourth R-wave 245 and fifth R-wave 245 in portion 225 may represent a different localized R-wave frequency 215-b. R-wave frequencies from 215-a or 215-b may be used to determine a patient's respiratory rate based on the RSA phenomenon described above. However, in some cases, due to patient variability, R-wave frequency 215-a and R-wave frequency 215-b may be the same (e.g., no RSA may be exhibited).

A second portion 230 of the ECG signal may represent a patient breathing with or against resistance (e.g., breathing with an increase in respiratory effort). For example, an increase in respiratory effort may be caused by coughing, wheezing, exercise, or a combination thereof. Diseases such as pneumonia, asthma, COPD, sleep anemia, and pulmonary edema may also cause an increase in respiratory effort. Changes in the level of respiratory effort may be indicated by patterns in the ECG signal. For example, an increase in amplitude modulation of the R-waves 245 may be detected between an R-wave amplitude 210-a of a first plurality of R-waves from the first portion 225 and an R-wave amplitude 210-b of a second plurality of R-waves from the second portion 230. As shown in plot 200, the R-wave amplitude 210-b of the second plurality of R-waves is greater than the R-wave amplitude 210-a of the first plurality of R-waves. This change in R-wave amplitude modulation between the first plurality of R-waves in the first portion 225 and the second plurality of R-waves in the second portion 230 may be indicative of an increase in respiratory effort in the second portion 230 as compared to the first portion 225. In other words, the increase in the distance between the maximum and minimum R-wave amplitude (e.g., an increase in modulation strength) may be indicative of an increase in respiratory effort. However, in some cases, R-wave amplitude 210-a and R-wave amplitude 210-b may be the same. That is, in some cases, due to patient variability, there may be no change in amplitude modulation exhibited.

In a similar fashion, modulations in R-wave frequency may indicate an increase in respiratory effort from portion 225 to portion 230. For example, as shown in the plot 200, there is an increase in the R-wave frequency modulation from portion 225 to the R-wave frequency modulation in portion 230. That is, the difference between R-wave frequency 215-d and R-wave frequency 215-c in portion 230 may be greater than the difference between R-wave frequency 215-b and R-wave frequency 215-a in portion 225. In some cases, R-wave frequency 215-c and R-wave frequency 215-a may represent localized maximum R-wave frequencies, whereas R-wave frequency 215-d and R-wave frequency 215-b may represent localized minimum R-wave frequencies. This change in frequency modulation may indicate that the patient is breathing with resistance (e.g., an increase in respiratory effort) during the second portion 230 as compared to portion 225.

A modulation in the baseline of the ECG signal may also be detected between the first portion 225 of the ECG signal and the second portion 230. As shown in the plot 200, the baseline of the ECG signal may be higher in portion 230 than in portion 225, which may also indicate an increase in respiratory effort during portion 230 as compared to portion 225. The changes in frequency, amplitude, and baseline modulation between portions 225 and 230 described above may be used in any combination to indicate changes in respiratory effort of a patient.

A third portion 235 of the ECG signal may represent a patient's respiratory pattern in response to titration of a drug. As described herein, a drug may be titrated (either automatically by a system or manually by a clinician) based on the change in respiratory effort calculated from the increase in modulation strength between the first portion 225 and the second portion 230. The patient's response to the titrated drug may be indicated in the ECG plot 200 as a decrease in respiratory effort in portion 235 as compared to portion 230. For example, as illustrated in plot 200, the R-wave amplitude 210-c of the third plurality of R-waves may be less than the R-wave amplitude 210-b of the second plurality of R-waves. In addition, there may be a change in the R-wave frequency modulation in portion 235 to the R-wave frequency modulation in portion 230. For example, the difference between R-wave frequency 215-f (e.g., distance between sixth R-wave 245 and seventh R-wave 245 in portion 235) and R-wave frequency 215-e (e.g., distance between first R-wave 245 and second R-wave 245 in portion 235) in portion 235 may be less than the difference between R-wave frequency 215-d and R-wave frequency 215-c in portion 230.

A fourth portion 240 of the ECG signal may represent a patient breathing without a resistance (e.g., a return normal breathing) after the drug is titrated. That is, the fourth portion 240 of the ECG signal may exhibit similar ECG patterns as the first portion 225 of the ECG signal.

Figure 3:
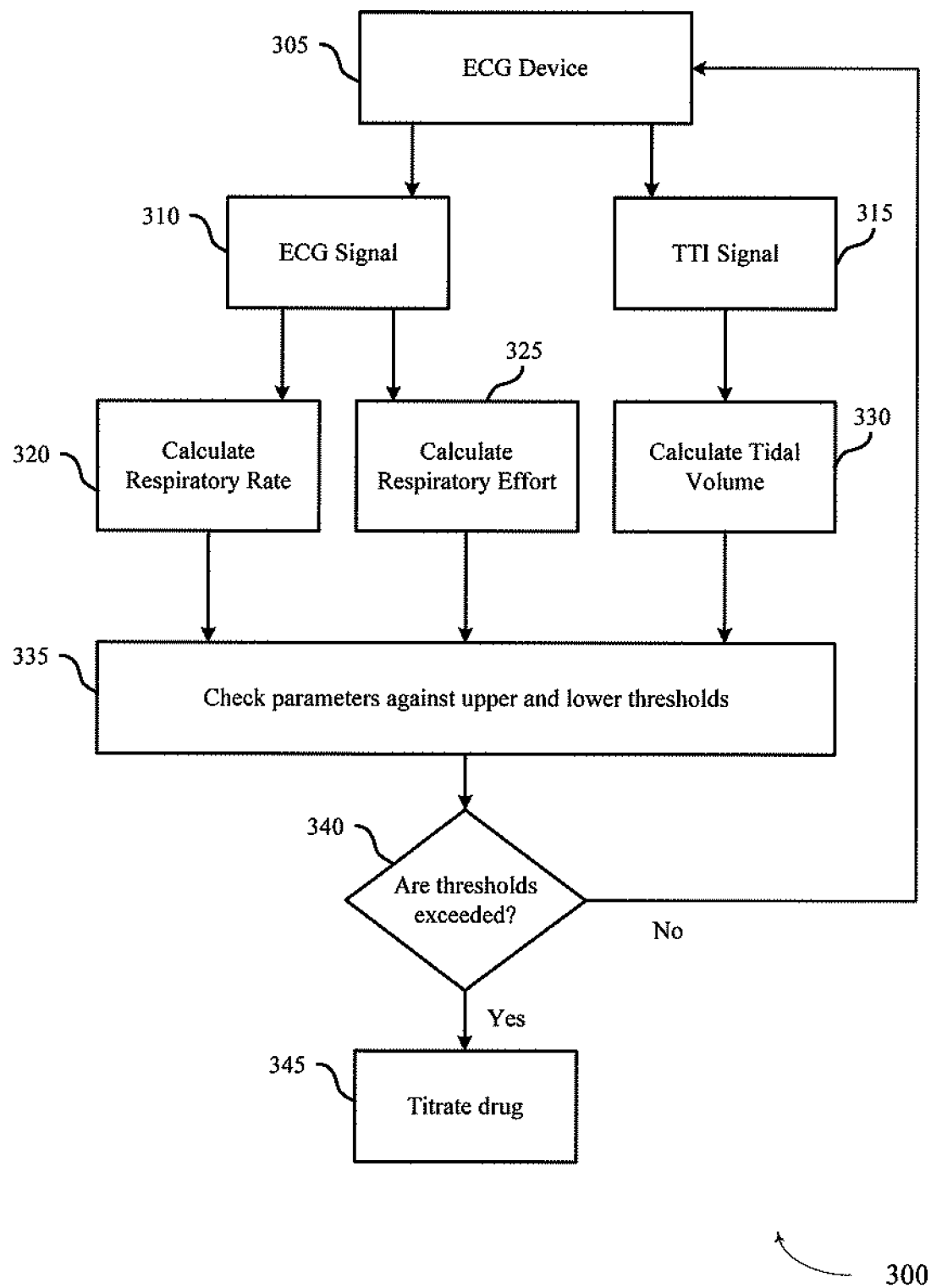
FIG. 3 shows a flowchart illustrating a method that supports measuring respiratory parameters from an ECG device in accordance with aspects of the present disclosure.

FIG. 3 shows a flowchart illustrating a method 300 for measuring respiratory parameters from an ECG device in accordance with various aspects of the present disclosure. The operations of method 300 may be implemented by any device or its components as described herein. For example, the operations of method 300 may be performed by a patient monitoring device or a system of devices as described with reference to FIG. 1 and FIGS. 4-7. In some examples, a device may execute a set of codes to control the functional elements of the device to perform the functions described below. Additionally or alternatively, the device may perform aspects of the functions described below using special-purpose hardware.

The operations of block 305 may be performed according to the methods described with reference to FIGS. 1 and 2. In certain examples, aspects of the operations of block 305 may be performed by an ECG device. For example, at block 305, an ECG device may be attached to a patient with one or more leads and may measure electrical signals caused by the heart beating.

At block 310, the ECG device may output an ECG signal for analysis as described with reference to FIG. 2. At block 315, the ECG device may produce a TTI signal (e.g., a measure of the patient's TTI may be determined from the leads of the ECG device). In some cases, a patient monitoring system as described with reference to FIG. 1 may receive an ECG signal and a TTI signal associated with a patient. The operations of blocks 310 and 315 may be performed according to the methods described with reference to FIGS. 1 and 2.

At block 320, the respiratory rate of the patient may be calculated or determined based on the ECG signal as described with reference to FIG. 2. At block 325, the respiratory effort of the patient may be calculated or determined based on the ECG signal. For example, a respiratory effort measure of the patient may be determined based on a change in respiratory effort from one period of time to another.

At block 330, the TV of the patient may be calculated or determined based on the TTI signal. Accordingly, a change in a patient's TV over time may be based on the TTI signal. The operations of blocks 320, 325, and 330 may be performed according to the methods described with reference to FIGS. 1 and 2.

At block 335, the device may analyze the parameters for respiratory rate, respiratory effort, and TV by comparing them against upper and lower thresholds. For example, the device may compare changes in respiratory effort against a predetermined respiratory effort threshold. As described with reference to FIG. 2, a change in a respiratory condition of the patient may be determined based on the comparison of one or multiple of the respiratory parameters.

At block 340, the device may determine if one or more of the thresholds (e.g., respiratory effort threshold, respiratory rate threshold, or TV threshold) are exceeded. If the thresholds are not exceeded, the method 300 may proceed to block 305. If one or more of the thresholds are exceeded, the method 300 may proceed to block 345. Accordingly, the device may determine whether to titrate or administer a drug to the patient or transmit an alert indicating the change in respiratory condition.

At block 345, the device may titrate a drug. The drug may be automatically or manually administered based on the determination (e.g., based on a diagnosis of a particular respiratory condition or disease status). In addition, the device may trigger an alarm indicating the change in respiratory effort of the patient. The operations of blocks 335, 340, and 345 may be performed according to the methods described with reference to FIGS. 1 and 2.

Figure 4:
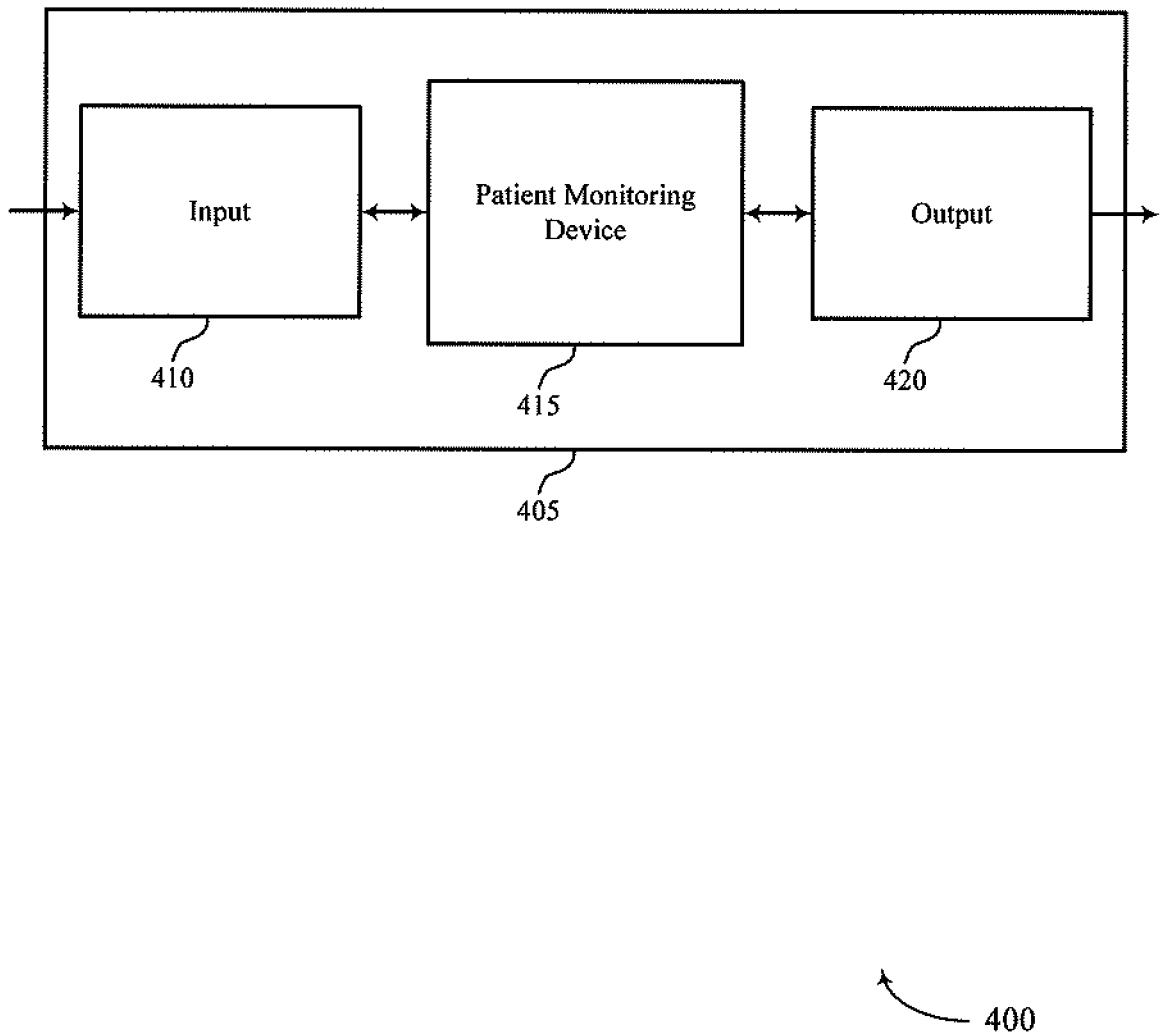
FIGS. 4 through 6 illustrates block diagrams of a device that supports measuring respiratory parameters from an ECG device in accordance with aspects of the present disclosure.

FIG. 4 illustrates a block diagram 400 of a device 405 that supports measuring respiratory parameters from an ECG device in accordance with aspects of the present disclosure. Device 405 may be an example of aspects of a medical device 110 as described herein. Device 405 may include input 410, patient monitoring device 415, and output 420. Device 405 may also include a processor. Each of these components may be in communication with one another (e.g., via one or more buses).

In embodiments where device 405 is an example or component of a medical device 110, input 410 may include or be associated with one or more sensor units configured to detect one or more physiological parameters of a patient wearing or holding the device 405. For example, input 410 may receive or detect respiratory data and/or non-respiratory physiological data associated with the patient, such as ECG data indicating a respiration rate, or accelerometer data indicating patient movement, among others.

In other embodiments, where device 405 is an example or component of a local or remote computing device or a central station as described with respect to FIG. 1, input 410 may indirectly receive one or more physiological parameters of a patient, such as respiratory data and/or non-respiratory physiological data. For example, input 410 may receive physiological data via caregiver input at a central nurses station, or may receive physiological data remotely transmitted from a patient-worn medical device.

Patient monitoring device 415 and/or at least some of its various sub-components may be implemented in hardware, software executed by a processor, firmware, or any combination thereof. If implemented in software executed by a processor, the functions of the patient monitoring device 415 and/or at least some of its various sub-components may be executed by a general-purpose processor, a digital signal processor (DSP), an application-specific integrated circuit (ASIC), an field-programmable gate array (FPGA) or other programmable logic device, discrete gate or transistor logic, discrete hardware components, or any combination thereof designed to perform the functions described in the present disclosure. The patient monitoring device 415 and/or at least some of its various sub-components may be physically located at various positions, including being distributed such that portions of functions are implemented at different physical locations by one or more physical devices. In some examples, patient monitoring device 415 and/or at least some of its various sub-components may be a separate and distinct component in accordance with various aspects of the present disclosure. In other examples, patient monitoring device 415 and/or at least some of its various sub-components may be combined with one or more other hardware components, including but not limited to an I/O component, a transceiver, a network server, another computing device, one or more other components described in the present disclosure, or a combination thereof in accordance with various aspects of the present disclosure.

Patient monitoring device 415 may receive an ECG signal associated with a patient, detect a change in modulation of the ECG signal between a first portion of the ECG signal and a second portion of the ECG signal, and determine a change in respiratory effort of the patient based on the change in modulation.

Output 420 may collect the change in respiratory effort of the patient from patient monitoring device 415 and communicate that change in respiratory effort to the caregiver or to another component in a system. In examples where device 405 is an example of a medical device, the change in respiratory effort may be displayed at the medical device using output 420 in some examples, or in other examples output 420 may communicate the change in respiratory effort to a local or remote computing device or central station. In other examples, where device 405 is an example of a local or remote computing device, or a central station, output 420 may display the change in respiratory effort locally at device 405.

Figure 5:
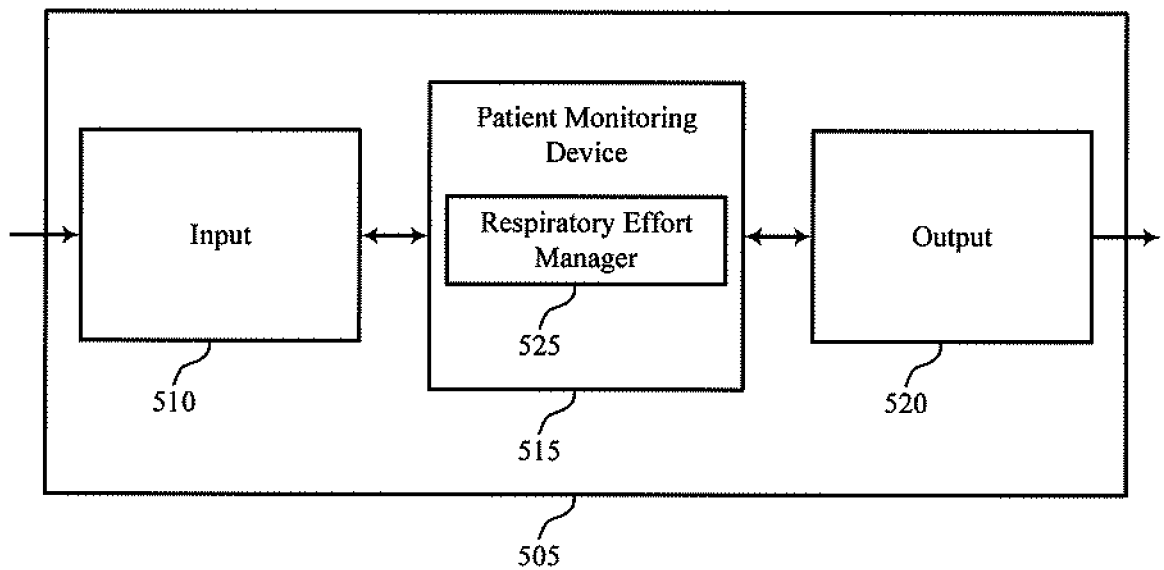

FIG. 5 illustrates a block diagram 500 of a device 505 that supports measuring respiratory parameters from an ECG device in accordance with aspects of the present disclosure. Device 505 may be an example of aspects of a device 405 with reference to FIG. 4. Device 505 may include input 510, patient monitoring device 515, output 520, and respiratory effort manager 525. Device 505 may also include a processor. Each of these components may be in communication with one another (e.g., via one or more buses).

Patient monitoring device 515 may be an example of aspects of the patient monitoring device 415 described with reference to FIG. 4. Patient monitoring device 515 may also include respiratory effort manager 525.

Respiratory effort manager 525 may receive an ECG signal associated with a patient, detect a change in modulation of the ECG signal between a first portion of the ECG signal and a second portion of the ECG signal, and determine a change in respiratory effort of the patient based on the change in modulation. In some cases, respiratory effort manager 525 may detect an increase in modulation strength in the second portion of the ECG signal and determine an increase in respiratory effort by the patient based on the increase in modulation strength. Respiratory effort manager 525 may determine a respiratory effort measure of the patient based on the change in respiratory effort, compare the respiratory effort measure to a predetermined respiratory effort threshold, and determine a change in a respiratory condition of the patient based on the comparison. In some examples, respiratory effort manager 525 may determine whether to administer a drug to the patient based on the comparison, automatically administer the drug based on the determination, and trigger an alarm indicating the change in respiratory effort of the patient.

Output 520 may be an example of output 420 as described in more detail with respect to FIG. 4. For example, output 520 may communicate the change in respiratory effort of the patient to a caregiver at or remotely from device 505.

Figure 6:
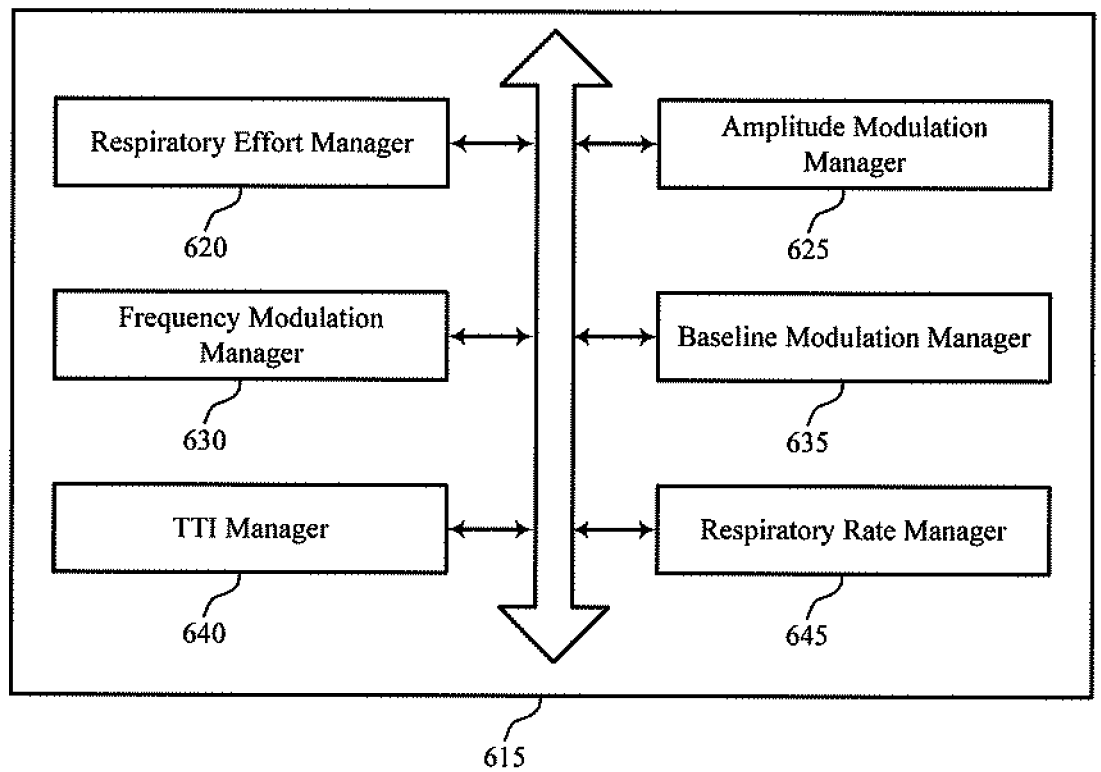

FIG. 6 illustrates a block diagram 600 of a patient monitoring device 615 that supports measuring respiratory parameters from an ECG device in accordance with aspects of the present disclosure. The patient monitoring device 615 may be an example of aspects of a patient monitoring device 515, or a patient monitoring device 715 described with reference to FIGS. 5, and 7. The patient monitoring device 615 may include respiratory effort manager 620, amplitude modulation manager 625, frequency modulation manager 630, baseline modulation manager 635, TTI manager 640, and respiratory rate manager 645. Each of these modules may communicate, directly or indirectly, with one another (e.g., via one or more buses).

Respiratory effort manager 620 may receive an ECG signal associated with a patient, detect a change in modulation of the ECG signal between a first portion of the ECG signal and a second portion of the ECG signal, and determine a change in respiratory effort of the patient based on the change in modulation. In some cases, respiratory effort manager 620 may detect an increase in modulation strength in the second portion of the ECG signal and determine an increase in respiratory effort by the patient based on the increase in modulation strength. Respiratory effort manager 620 may determine a respiratory effort measure of the patient based on the change in respiratory effort, compare the respiratory effort measure to a predetermined respiratory effort threshold, and determine a change in a respiratory condition of the patient based on the comparison. In some examples, respiratory effort manager 620 may determine whether to administer a drug to the patient based on the comparison, automatically administer the drug based on the determination, and trigger an alarm indicating the change in respiratory effort of the patient.

Amplitude modulation manager 625 may detect the change in modulation that includes comparing an R-wave amplitude modulation of a first set of R-waves from the first portion of the ECG signal with an R-wave amplitude modulation of a second set of R-waves from the second portion of the ECG signal. In some cases, the R-wave amplitude modulation of the second set of R-waves is greater than the R-wave amplitude modulation of the first set of R-waves.

Frequency modulation manager 630 may detect the change in modulation that includes comparing a frequency modulation of a first set of R-waves from the first portion of the ECG signal with a frequency modulation of a second set of R-waves from the second portion of the ECG signal. In some cases, frequency modulation manager 630 may detect that a difference between a maximum R-wave frequency and a minimum R-wave frequency in the second portion of the ECG signal is greater than a difference between a maximum R-wave frequency and a minimum R-wave frequency in the first portion of the ECG signal.

Baseline modulation manager 635 may detect the change in modulation that includes comparing a baseline of a first set of R-waves from the first portion of the ECG signal with a baseline of a second set of R-waves from the second portion of the ECG signal.

TTI manager 640 may determine a TTI of the patient based on the ECG signal, determine a change in a tidal volume of the patient based on the TTI, and determine the change in the respiratory condition of the patient is based on the change in the tidal volume.

Respiratory rate manager 645 may determine a respiratory rate of the patient based on the ECG signal, compare the respiratory rate to a predetermine respiratory rate threshold, and determine the change in the respiratory condition of the patient is based on the respiratory rate.

Figure 7:
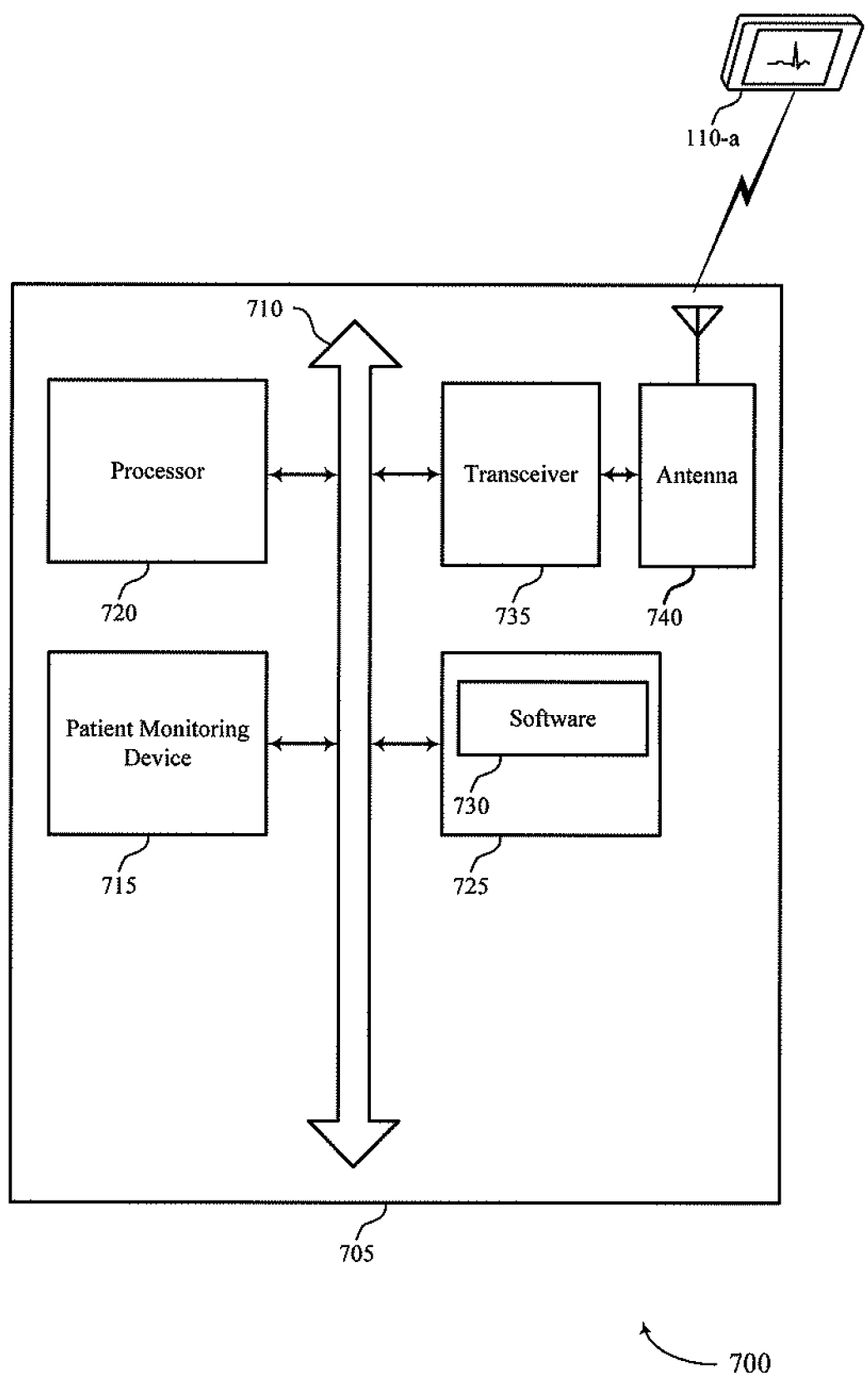
FIG. 7 illustrates a block diagram of a system including a device that supports measuring respiratory parameters from an ECG device in accordance with aspects of the present disclosure.

FIG. 7 illustrates a block diagram of a system 700 including a device 705 that supports measuring respiratory parameters from an ECG device in accordance with aspects of the present disclosure. Device 705 may be an example of or include the components of device 405, 505, and 605 as described above, e.g., with reference to FIGS. 4, 5, and 6. Device 705 may include components for bi-directional voice and data communications including components for transmitting and receiving communications, including patient monitoring device 715, processor 720, memory 725, software 730, transceiver 735, and one or more antennas 740. These components may be in electronic communication via one or more buses (e.g., bus 710).

Processor 720 may include an intelligent hardware device, e.g., a CPU, a microcontroller, an ASIC, etc. The processor 720 may process information received from medical device 110-a. The processor 720 may also process information to be transmitted to one or more remote modules via transceiver 735 and antenna 740. Communications received at or transmitted from the transceiver 735 may be received from or transmitted to medical device 110 or local computing devices 115, 120 via a network.

Memory 725 may include RAM and/or ROM. The server memory 725 may store computer-readable, computer-executable code (SW) 730 containing instructions that are configured to, when executed, cause the processor 720 to perform various functions described herein related to monitoring patient respiration. Alternatively, the code 730 may not be directly executable by the processor 720 but may be configured to cause the medical device 110 (e.g., when compiled and executed) to perform various of the functions described herein.

Software 730 may include code to implement aspects of the present disclosure, including code to support measuring respiratory parameters from an ECG device. Software 730 may be stored in a non-transitory computer-readable medium such as system memory or other memory. In some cases, the software 730 may not be directly executable by the processor but may cause a computer (e.g., when compiled and executed) to perform functions described herein.

Transceiver 735 may communicate bi-directionally, via one or more antennas 740, wired, or wireless links as described above. For example, the transceiver 735 may represent a wireless transceiver and may communicate bi-directionally with another wireless transceiver. The transceiver 735 may also include a modem to modulate the packets and provide the modulated packets to the antennas for transmission, and to demodulate packets received from the antennas 740.

Figure 8:
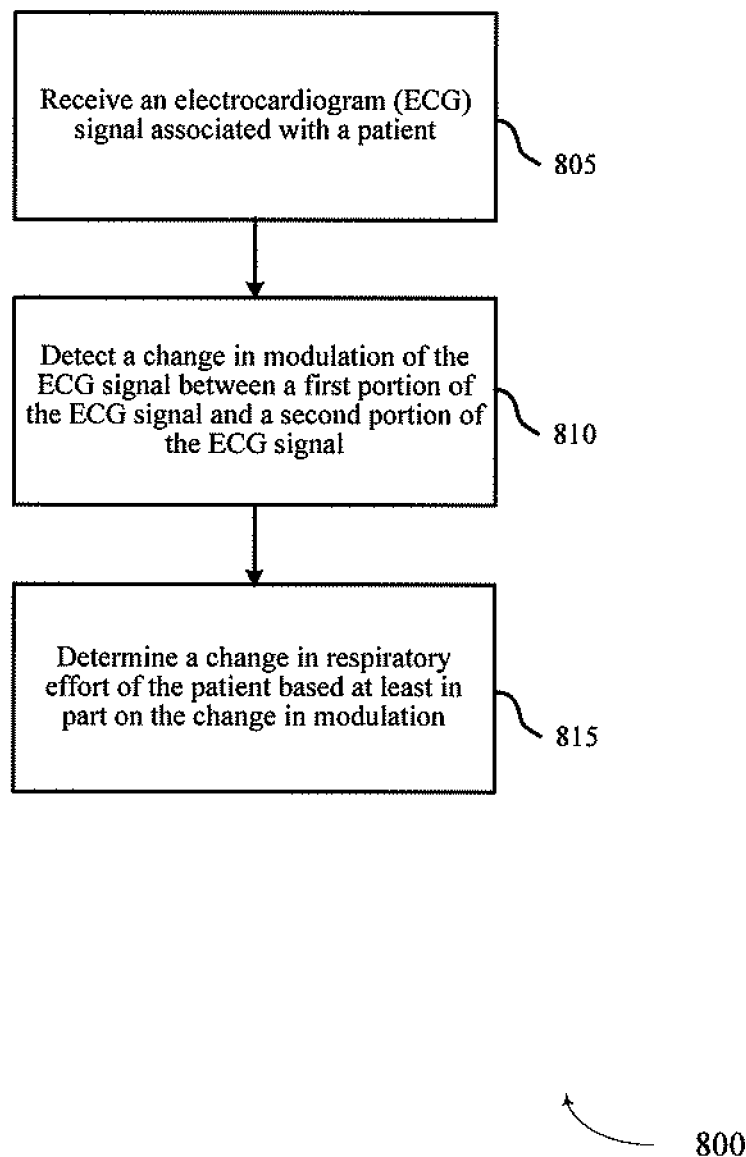
FIGS. 8 through 12 illustrate methods for measuring respiratory parameters from an ECG device in accordance with aspects of the present disclosure.

FIG. 8 illustrates method 800 for measuring respiratory parameters from an ECG device in accordance with various aspects of the present disclosure. The operations of method 800 may be implemented by a device or its components as described herein. In some examples, a device may execute a set of codes to control the functional elements of the device to perform the functions described below. Additionally or alternatively, the device may perform aspects the functions described below using special-purpose hardware.

At block 805 the method may include receiving an ECG signal associated with a patient. The operations of block 805 may be performed according to the methods described with reference to FIGS. 1-7.

At block 810 the method may include detecting a change in modulation of the ECG signal between a first portion of the ECG signal and a second portion of the ECG signal. In some cases, detecting a change in modulation includes comparing an R-wave amplitude modulation of a first plurality of R-waves from the first portion of the ECG signal with an R-wave amplitude modulation of a second plurality of R-waves from the second portion of the ECG signal. Detecting a change in modulation may, in some cases, include comparing a frequency modulation of a first plurality of R-waves from the first portion of the ECG signal with a frequency modulation of a second plurality of R-waves from the second portion of the ECG signal. In some applications, detecting a change in modulation includes comparing a baseline of a first plurality of R-waves from the first portion of the ECG signal with a baseline of a second plurality of R-waves from the second portion of the ECG signal. The operations of block 810 may be performed according to the methods described with reference to FIGS. 1-7.

At block 815 the method may include determining a change in respiratory effort of the patient based at least in part on the change in modulation. The operations of block 815 may be performed according to the methods described with reference to FIGS. 1-7.

Figure 9:
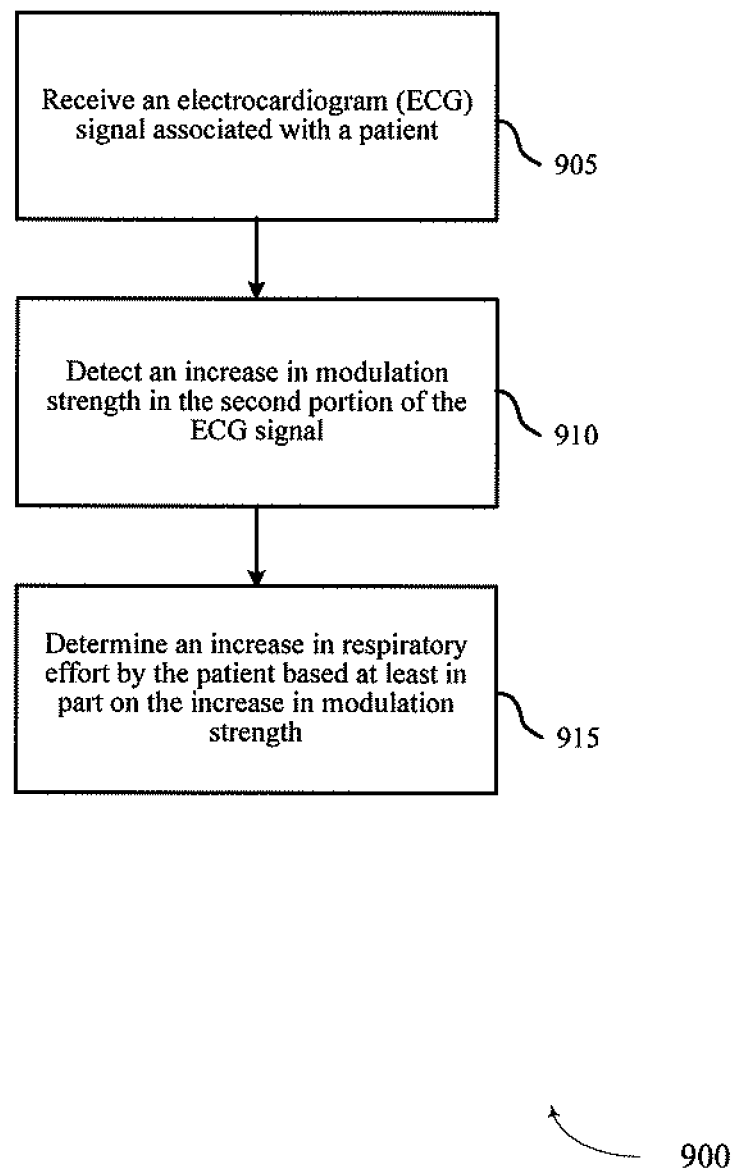

FIG. 9 illustrates method 900 for measuring respiratory parameters from an ECG device in accordance with various aspects of the present disclosure. The operations of method 900 may be implemented by a device or its components as described herein. In some examples, a device may execute a set of codes to control the functional elements of the device to perform the functions described below. Additionally or alternatively, the device may perform aspects the functions described below using special-purpose hardware.

At block 905 the method may include receiving an ECG signal associated with a patient. The operations of block 905 may be performed according to the methods described with reference to FIGS. 1-7.

At block 910, the method may include detecting an increase in modulation strength in the second portion of the ECG signal. The increase in modulation strength may be detected by detecting a change in modulation of the ECG signal between a first portion of the ECG signal and a second portion of the ECG signal. In some cases, detecting a change in modulation includes comparing an R-wave amplitude modulation of a first plurality of R-waves from the first portion of the ECG signal with an R-wave amplitude modulation of a second plurality of R-waves from the second portion of the ECG signal. Detecting a change in modulation may, in some cases, include comparing a frequency modulation of a first plurality of R-waves from the first portion of the ECG signal with a frequency modulation of a second plurality of R-waves from the second portion of the ECG signal. In some applications, detecting a change in modulation includes comparing a baseline of a first plurality of R-waves from the first portion of the ECG signal with a baseline of a second plurality of R-waves from the second portion of the ECG signal. The operations of block 910 may be performed according to the methods described with reference to FIGS. 1-7.

At block 915, the method may include determining an increase in respiratory effort by the patient based at least in part on the increase in modulation strength. The operations of block 915 may be performed according to the methods described with reference to FIGS. 1-7.

Figure 10:
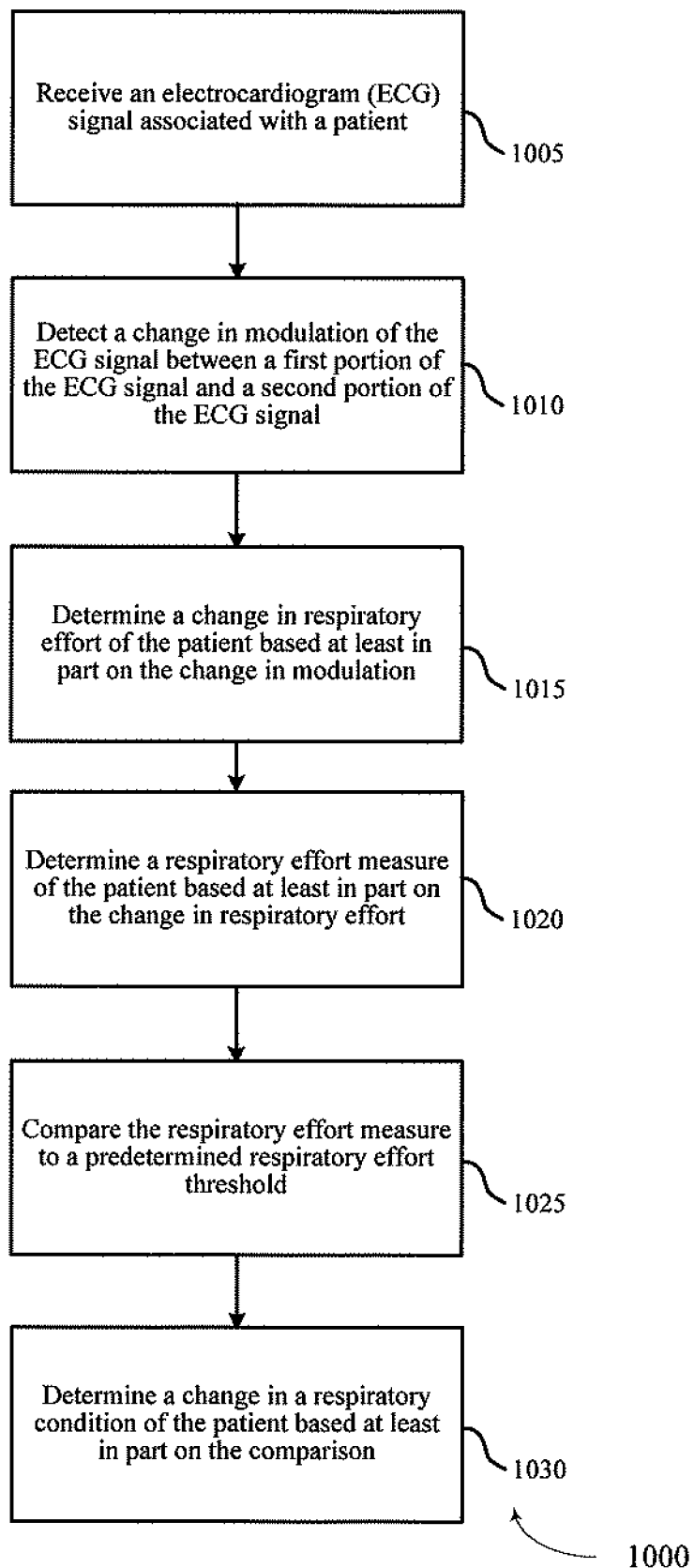

FIG. 10 illustrates method 1000 for measuring respiratory parameters from an ECG device in accordance with various aspects of the present disclosure. The operations of method 1000 may be implemented by a device or its components as described herein. In some examples, a device may execute a set of codes to control the functional elements of the device to perform the functions described below. Additionally or alternatively, the device may perform aspects the functions described below using special-purpose hardware.

At block 1005 the method may include receiving an ECG signal associated with a patient. The operations of block 1005 may be performed according to the methods described with reference to FIGS. 1-7.

At block 1010 the method may include detecting a change in modulation of the ECG signal between a first portion of the ECG signal and a second portion of the ECG signal. In some cases, detecting a change in modulation includes comparing an R-wave amplitude modulation of a first plurality of R-waves from the first portion of the ECG signal with an R-wave amplitude modulation of a second plurality of R-waves from the second portion of the ECG signal. Detecting a change in modulation may, in some cases, include comparing a frequency modulation of a first plurality of R-waves from the first portion of the ECG signal with a frequency modulation of a second plurality of R-waves from the second portion of the ECG signal. In some applications, detecting a change in modulation includes comparing a baseline of a first plurality of R-waves from the first portion of the ECG signal with a baseline of a second plurality of R-waves from the second portion of the ECG signal. The operations of block 1010 may be performed according to the methods described with reference to FIGS. 1-7.

At block 1015 the method may include determining a change in respiratory effort of the patient based at least in part on the change in modulation. The operations of block 1015 may be performed according to the methods described with reference to FIGS. 1-7. At block 1020, the method may include determining a respiratory effort measure of the patient based at least in part on the change in respiratory effort. At block 1025, the method may include comparing the respiratory effort measure to a predetermined respiratory effort threshold. At block 1030, the method may include determining a change in a respiratory condition of the patient based at least in part on the comparison. Determining a change in a respiratory condition may include detecting the onset or progression of a respiratory disease or condition as described above.

Figure 11:
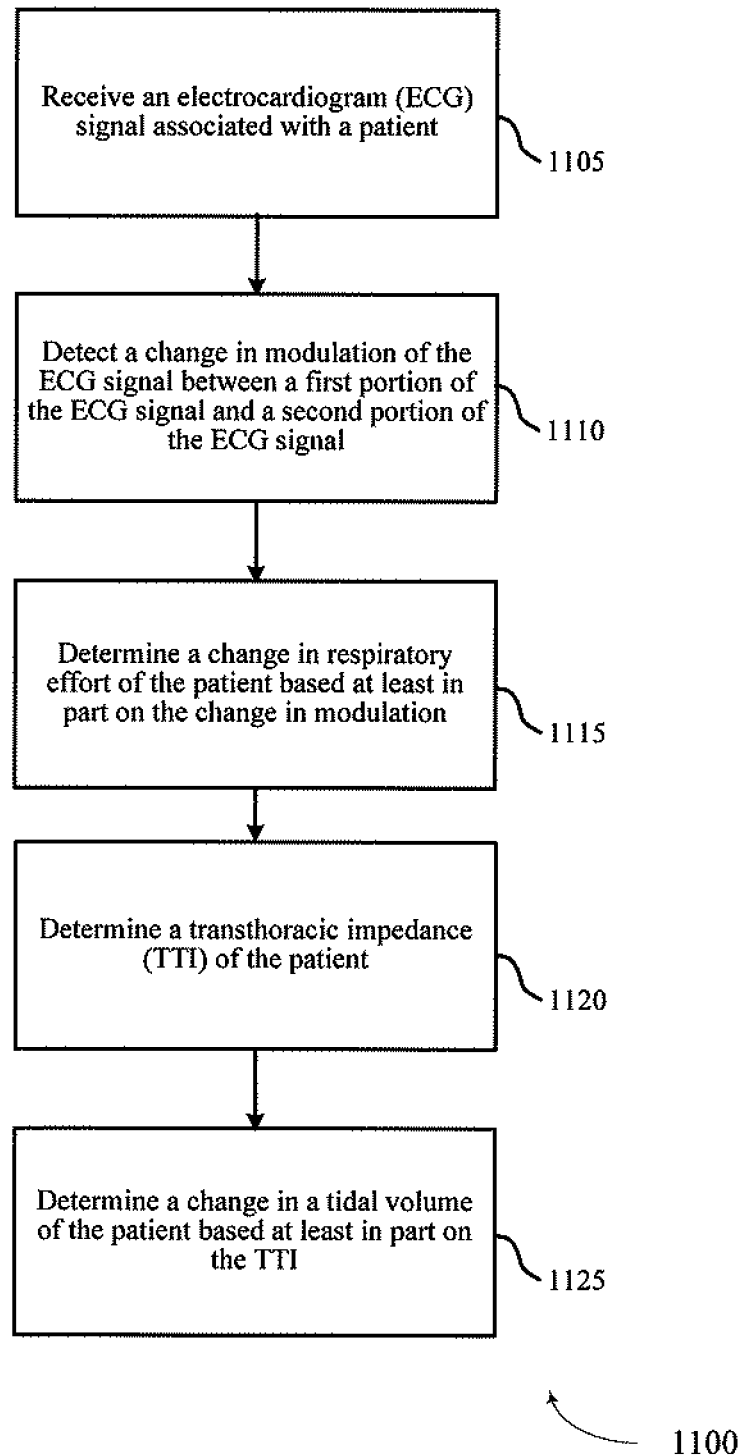

FIG. 11 illustrates method 1100 for measuring respiratory parameters from an ECG device in accordance with various aspects of the present disclosure. The operations of method 1100 may be implemented by a device or its components as described herein. In some examples, a device may execute a set of codes to control the functional elements of the device to perform the functions described below. Additionally or alternatively, the device may perform aspects the functions described below using special-purpose hardware.

At block 1105 the method may include receiving an ECG signal associated with a patient. The operations of block 1105 may be performed according to the methods described with reference to FIGS. 1-7.

At block 1110 the method may include detecting a change in modulation of the ECG signal between a first portion of the ECG signal and a second portion of the ECG signal. In some cases, detecting a change in modulation includes comparing an R-wave amplitude modulation of a first plurality of R-waves from the first portion of the ECG signal with an R-wave amplitude modulation of a second plurality of R-waves from the second portion of the ECG signal. Detecting a change in modulation may, in some cases, include comparing a frequency modulation of a first plurality of R-waves from the first portion of the ECG signal with a frequency modulation of a second plurality of R-waves from the second portion of the ECG signal. In some applications, detecting a change in modulation includes comparing a baseline of a first plurality of R-waves from the first portion of the ECG signal with a baseline of a second plurality of R-waves from the second portion of the ECG signal. The operations of block 1110 may be performed according to the methods described with reference to FIGS. 1-7.

At block 1115 the method may include determining a change in respiratory effort of the patient based at least in part on the change in modulation. The operations of block 1115 may be performed according to the methods described with reference to FIGS. 1-7. At block 1120, the method may include determining a TTI of the patient. At block 1125, the method may include determining a change in a tidal volume of the patient based at least in part on the TTI. In some cases, determining the change in the respiratory condition of the patient is based at least in part on the change in the tidal volume.

Figure 12:
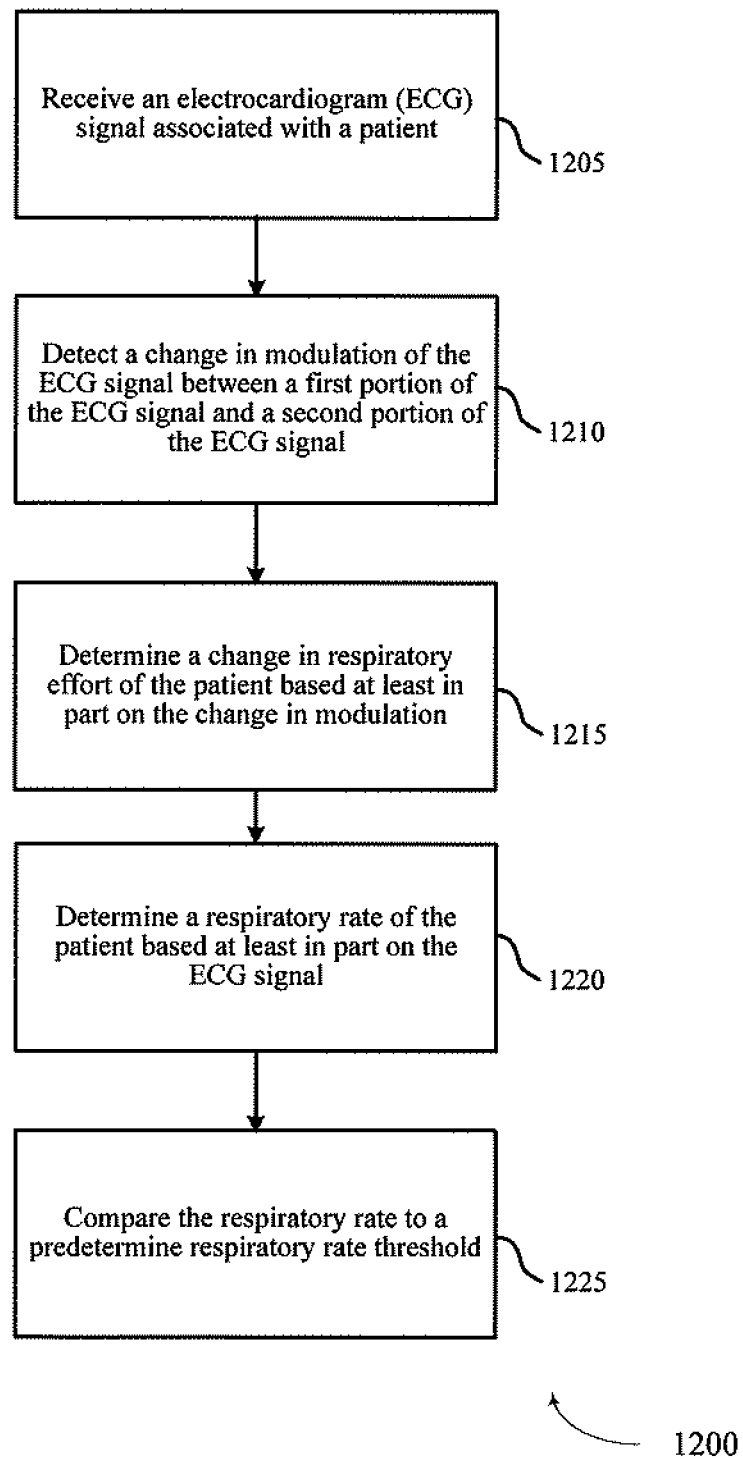

FIG. 12 illustrates method 1200 for measuring respiratory parameters from an ECG device in accordance with various aspects of the present disclosure. The operations of method 1200 may be implemented by a device or its components as described herein. In some examples, a device may execute a set of codes to control the functional elements of the device to perform the functions described below. Additionally or alternatively, the device may perform aspects the functions described below using special-purpose hardware.

At block 1205 the method may include receiving an ECG signal associated with a patient. The operations of block 1205 may be performed according to the methods described with reference to FIGS. 1-7.

At block 1210 the method may include detecting a change in modulation of the ECG signal between a first portion of the ECG signal and a second portion of the ECG signal. In some cases, detecting a change in modulation includes comparing an R-wave amplitude modulation of a first plurality of R-waves from the first portion of the ECG signal with an R-wave amplitude modulation of a second plurality of R-waves from the second portion of the ECG signal. Detecting a change in modulation may, in some cases, include comparing a frequency modulation of a first plurality of R-waves from the first portion of the ECG signal with a frequency modulation of a second plurality of R-waves from the second portion of the ECG signal. In some applications, detecting a change in modulation includes comparing a baseline of a first plurality of R-waves from the first portion of the ECG signal with a baseline of a second plurality of R-waves from the second portion of the ECG signal. The operations of block 1210 may be performed according to the methods described with reference to FIGS. 1-7.

At block 1215 the method may include determining a change in respiratory effort of the patient based at least in part on the change in modulation. The operations of block 1215 may be performed according to the methods described with reference to FIGS. 1-7. At block 1220, the method may include determining a respiratory rate of the patient based at least in part on the ECG signal. At block 1225, the method may include comparing the respiratory rate to a predetermine respiratory rate threshold. In some cases, determining the change in the respiratory condition of the patient is based at least in part on the respiratory rate.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, an field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C).

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method of patient monitoring, comprising:
   receiving an electrocardiogram (ECG) signal associated with a patient;
   detecting a change in an amplitude modulation of the ECG signal between a first portion of the ECG signal and a second portion of the ECG signal, wherein the first portion corresponds to the patient breathing without resistance and the second portion corresponds to the patient breathing with resistance; and
   determining a change in respiratory effort of the patient based at least in part on the change in the amplitude modulation between the first portion and the second portion.

2. The method of claim 1, wherein detecting the change in the amplitude modulation comprises comparing an R-wave amplitude modulation of a first plurality of R-waves from the first portion of the ECG signal with an R-wave amplitude modulation of a second plurality of R-waves from the second portion of the ECG signal.

3. The method of claim 2, wherein the R-wave amplitude modulation of the second plurality of R-waves is greater than the R-wave amplitude modulation of the first plurality of R-waves.

4. The method of claim 1, further comprising:
   detecting an increase in modulation strength in the second portion of the ECG signal; and
   determining an increase in respiratory effort by the patient based at least in part on the increase in modulation strength.

5. The method of claim 1, further comprising:
   determining a respiratory effort measure of the patient based at least in part on the change in respiratory effort;

comparing the respiratory effort measure to a predetermined respiratory effort threshold; and
determining a change in a respiratory condition of the patient based at least in part on the comparison.

6. The method of claim 5, further comprising:
determining a transthoracic impedance (TTI) of the patient based at least in part on the ECG signal;
determining a change in a tidal volume of the patient based at least in part on the TTI; and
wherein determining the change in the respiratory condition of the patient is based at least in part on the change in the tidal volume.

7. The method of claim 5, further comprising:
determining a respiratory rate of the patient based at least in part on the ECG signal;
comparing the respiratory rate to a predetermine respiratory rate threshold; and
wherein determining the change in the respiratory condition of the patient is based at least in part on the respiratory rate.

8. The method of claim 5, further comprising:
determining whether to administer a drug to the patient based at least in part on the comparison; and
automatically administering or ceasing administration of the drug based at least in part on the determination.

9. The method of claim 1, further comprising:
triggering an alarm indicating the change in respiratory effort of the patient.

10. A medical device for patient monitoring, comprising:
a processor;
memory in electronic communication with the processor; and
instructions stored in the memory and operable, when executed by the processor, to cause the apparatus to:
receive an electrocardiogram (ECG) signal associated with a patient;
detect a change in an amplitude modulation of the ECG signal between a first portion of the ECG signal and a second portion of the ECG signal, wherein the first portion corresponds to the patient breathing without resistance and the second portion corresponds to the patient breathing with resistance; and
determine a change in respiratory effort of the patient based at least in part on the change in the amplitude modulation between the first portion and the second portion.

11. The apparatus of claim 10, wherein the instructions are further executable by the processor to:
compare an R-wave amplitude modulation of a first plurality of R-waves from the first portion of the ECG signal with an R-wave amplitude modulation of a second plurality of R-waves from the second portion of the ECG signal.

12. The apparatus of claim 10, wherein the instructions are further executable by the processor to:
detect an increase in modulation strength in the second portion of the ECG signal; and
determine an increase in respiratory effort by the patient based at least in part on the increase in modulation strength.

13. The apparatus of claim 10, wherein the instructions are further executable by the processor to:
determine a respiratory effort measure of the patient based at least in part on the change in respiratory effort;
compare the respiratory effort measure to a predetermined respiratory effort threshold; and
determine a change in a respiratory condition of the patient based at least in part on the comparison.

14. The apparatus of claim 13, wherein the instructions are further executable by the processor to:
determine a transthoracic impedance (TTI) of the patient;
determine a change in a tidal volume of the patient based at least in part on the TTI; and
wherein determining the change in the respiratory condition of the patient is based at least in part on the change in the tidal volume.

15. The apparatus of claim 13, wherein the instructions are further executable by the processor to:
determine a respiratory rate of the patient based at least in part on the ECG signal;
compare the respiratory rate to a predetermine respiratory rate threshold; and
wherein determining the change in the respiratory condition of the patient is based at least in part on the respiratory rate.

16. A non-transitory computer readable medium storing code for patient monitoring, the code comprising instructions executable by a processor to:
receive an electrocardiogram (ECG) signal associated with a patient;
detect a change in an amplitude modulation of the ECG signal between a first portion of the ECG signal and a second portion of the ECG signal, wherein the first portion corresponds to the patient breathing without resistance and the second portion corresponds to the patient breathing with resistance; and
determine a change in respiratory effort of the patient based at least in part on the change in the amplitude modulation between the first portion and the second portion.

* * * * *